United States Patent [19]

Lapidus

[11] Patent Number: 5,624,745
[45] Date of Patent: Apr. 29, 1997

[54] DENTAL ADHESIVE DEVICE AND METHOD FOR PRODUCING SAME

[75] Inventor: Herbert Lapidus, Ridgefield, Conn.

[73] Assignee: Combe Incorporated, White Plains, N.Y.

[21] Appl. No.: 476,280

[22] Filed: Jun. 7, 1995

[51] Int. Cl.$^6$ ........................................ B32B 5/26
[52] U.S. Cl. ...................... 428/308.8; 433/168.1; 433/180; 433/199.1; 156/275.7; 156/327
[58] Field of Search ............................ 433/168, 180.1, 433/199; 428/286, 290, 299, 300, 523; 156/275.7, 327

[56] References Cited

U.S. PATENT DOCUMENTS

| | | | |
|---|---|---|---|
| 2,978,812 | 4/1961 | Rosenthal et al. | |
| 3,868,340 | 2/1975 | Keegan et al. | 260/17.4 ST |
| 3,990,149 | 11/1976 | Nedig | 32/2 |
| 4,503,116 | 3/1985 | Lapidus | 428/286 |
| 4,632,880 | 12/1986 | Lapidus | 428/523 |
| 4,867,681 | 9/1989 | Knospins | 433/180 |
| 5,158,825 | 10/1992 | Alwirth | 428/286 |

FOREIGN PATENT DOCUMENTS

| | | | |
|---|---|---|---|
| 0407681 | 1/1991 | European Pat. Off. | A61K 6/00 |
| 35-46367 | 10/1988 | Germany | A61K 6/00 |
| 39-13005 | 2/1992 | Germany | A61C 13/23 |

*Primary Examiner*—Daniel Zirker
*Attorney, Agent, or Firm*—Fitzpatrick, Cella, Harper & Scinto

[57] ABSTRACT

An improved dental adhesive device to hold prosthetic devices in the human mouth is made as a laminate of webs which are bonded together by deforming a film of thermoplastic ethylene oxide polymer. The dental adhesive is produced by continuously applying a film of thermoplastic ethylene oxide polymer between moving webs of cellulose acetate fibers and then passing said webs in superimposed relationship between a pair of dry heated calendar rolls for thermoplastically bonding said webs into a unitary structure. A dry water-activated adhesive material, such as sodium alginate, may be employed with the thermoplastic ethylene oxide polymer by being dissolved or dispersed in the polymer film. Synthetic fibers are applied to the webs so as to extend transversely through the webs.

16 Claims, 5 Drawing Sheets

DENTAL ADHESIVE DEVICE AND METHOD FOR PRODUCING SAME

BACKGROUND OF THE INVENTION

1. Field of the Invention

The present invention relates to an improved device for fixing in place a prosthetic device in the human mouth and a method for producing the same.

2. Description of Related Art

A superior dental adhesive product has been commercially available under the trademark SEA-BOND® and is used in the human mouth to bond a denture to the soft gum tissues. As described in U.S. Pat. No. 4,503,116, the disclosure of which is incorporated herein by reference, the dental adhesive is a laminate of webs having a carrier portion with fibers thermoplastically bonded together by an interposed layer of ethylene oxide polymer powder. The ethylene oxide polymer powder is a dry, water-activated adhesive.

Accordingly, the plastic properties of the ethylene oxide polymer make a better laminate and its water-activated adhesive properties improve the laminate denture fixability. Such fixative properties are further improved by admixing another dry, water-activated adhesive material, such as sodium alginate, with the ethylene oxide polymer powder to promote formation of a gel-like adhesive mass between the denture plate and the mouth tissue.

To prepare the dental adhesive product, a fiber-faced web is formed by arranging a layer of loose synthetic fibers on a carrier such as a cellulosic paper. The loose fibers are passed through the carrier by needle-punching them so the fibers protrude from either side of the paper. A pair of such fiber-faced carriers are heat- and pressure-bonded together by the thermoplastic powder layer, such as ethylene oxide polymer powder to which a dry powder fixative, such as sodium alginate, has been added.

In the product of U.S. Pat. No. 4,503,116 as illustrated in FIG. 1, a pair of fiber-faced webs 10, 12 are formed and rolled into feed rolls 14, 16. One web roll is fed under an electrostatic powder spreader 18, which progressively applies a bonding agent 20 of powdered ethylene oxide polymer to the facing surface of web 10. The other web 12 is fed to be superimposed above and in contact with web 10 via idler roll 21 so the bonding agent 20 is spaced therebetween. The resulting web and powder sandwich 22 is fed into a nip of a pair of heated calendar rolls 24, 26 which are sufficiently heated to melt the powdered thermoplastic bonding agent in order to bond the web fibers into a unitary laminate 28 which is typically rolled up onto a core 30.

While the resulting product has enjoyed great commercial success, further improvements are desired.

When the powdered ethylene oxide is dispersed as a powder shower 20 from powder spreader 18, such as an Oxy-Dry electrostatic powder spreader, onto the fiber-faced web, certain nonuniformities in the dispersed powder sometimes occur. The powder can be dispersed to form a nonuniform powder layer with varying thickness across the web. This can affect the strength of the thermoplastic bond which is formed thereafter. Occasionally, the powder is dispersed as large agglomerates or clumps 19, which prevent complete fusion of webs 10 and 12 and rejection of the resulting laminate. Where the powder layer is of nonuniform thickness and/or clumps of powder are present, the resulting product produced contains portions which are not useable.

In addition, powder fines are present or are formed by handling commercially available ethylene oxide powder, such as polyox WSR-301 brand ethylene oxide polymer. When such powder is dispersed on the web, fines are released to create dust problems. The resulting polymer dust must be collected and/or eliminated from the manufacturing operation. The dust which is so removed is wasted to the process and its removal increases equipment needs, the energy cost and monitoring costs.

Moreover, the step of depositing a uniform layer of powder on a fiber-faced web is slower than the other manufacturing steps and it reduces the overall efficiency of the continuous process.

Finally, the ethylene oxide polymer powder must be admixed in the desired ratio with a water-activated adhesive powder such as sodium alginate, when that embodiment is employed. Typically, a ribbon mixer is so utilized. Additional equipment: and personnel are required to monitor this solids mixing operation to prevent similar problems with agglomerate formation and dust formation.

SUMMARY OF THE INVENTION

Accordingly, it is an object of the present invention to eliminate the manufacturing problems engendered by applying a powder form of ethylene oxide to a fibrous web in the process for producing a dental adhesive product.

It is another object to provide an improved dental adhesive product which shows improved bonding and eliminates waste during use.

These and other objects and advantages are obtained when an improved dental adhesive product is produced by applying a film comprising a thermoplastic ethylene oxide polymer to a surface of a first fibrous web. A second fibrous web is superimposed on the first web to sandwich the film therebetween. Heat and pressure are applied to deform the ethylene oxide polymer matrix and to thereby thermoplastically bond the webs into a unitary structure.

By employing a film of ethylene oxide sandwiched between superimposed fiber-faced webs, the problems associated with depositing ethylene oxide in powder form as a powder layer on a web are obviated. Since the ethylene oxide polymer is applied as a pre-cast film, not as a powder, dusting and clumping are obviated. The uniform ethylene oxide film forms an especially strong bond with the webs and fibers, which enhances its use fulness.

While ethylene oxide has been known as a water-activated adhesive, the invention contemplates advantageously using its thermoplastic and film-forming properties to make a better laminate for use in the mouth and to also use its recognized water-activated adhesive properties to improve the laminate's denture fixative abilities. Moreover, the fixative properties may be improved by dissolving additional water-activated adhesive material in the ethylene oxide polymer matrix or by dispersing insoluble additives such as gums, and the like, in the polymer matrix. This feature further promotes the formation of a gel-like adhesive mass between the denture plate and the mouth tissue.

The webs of the laminate may range from woven napped material, to an unwoven fiber or web such as a light polypropylene scrim or a cellulose paper, or to an unwoven fiber or web with cellulose acetate fibers bonded to said unwoven web as by needle punching. The method of producing the device involves progressively feeding one of said fiber-faced webs over spaced feed rolls, while applying a film of the ethylene oxide polymer either alone or having additional dissolved or dispersed water-activated additive therein, to the opposite surface of said web. The film supported on the web is then fed together with a second web in superimposed relation under a guide roll and then between a pair of heated calendar rolls, heated to about 210° F., for heating and pressure consolidation of the resultant laminated assembly.

The resultant laminated assembly is a dental adhesive laminate which has improved mechanical properties and when used will form a good seal between the gum and denture plate for long durations. The earlier problems of forming nonuniform powder layers, the clumping of dispersed ethylene oxide powder and formation of ethylene oxide polymer dust are overcome. Further, the application of a pre-cast continuous film to a continuous web is faster than the deposition of a powder layer on a continuous web. Moreover, there is exhibited enhanced uniformity for an adhesive or adhesive mixture cast from a solution as compared to an adhesive deposited by dry application of mixed powders.

It is also contemplated that synthetic fibers be applied to the webs so as to extend transversely through the webs. With the free ends of the fibers from each respective web thereby being caused to intermingle, an additional step of needle punching is employed to entangle and mechanically interlock the respective ends. Such a step may be employed just before the superimposed webs advance between the heated calendar rolls 24, 26. In this manner, even greater bonding between the webs is achieved by coupling the mechanical bonding of the fibers with that provided by the polymer binder and by the water-activated adhesive.

Another advantage of using a pre-cast continuous film is to enable the use of a non-needled web to obtain a thinner product. This will provide a different mouth feel or a better fit. A smooth surface now becomes available for bonding, whereas it is impractical to use powder to obtain a uniform layer.

The invention may be more completely understood by the following detailed description and the drawings of the preferred embodiment referred to therein.

BRIEF DESCRIPTION OF THE DRAWINGS

In the accompanying drawings.

DESCRIPTION OF THE PREFERRED EMBODIMENTS

Figure 1:
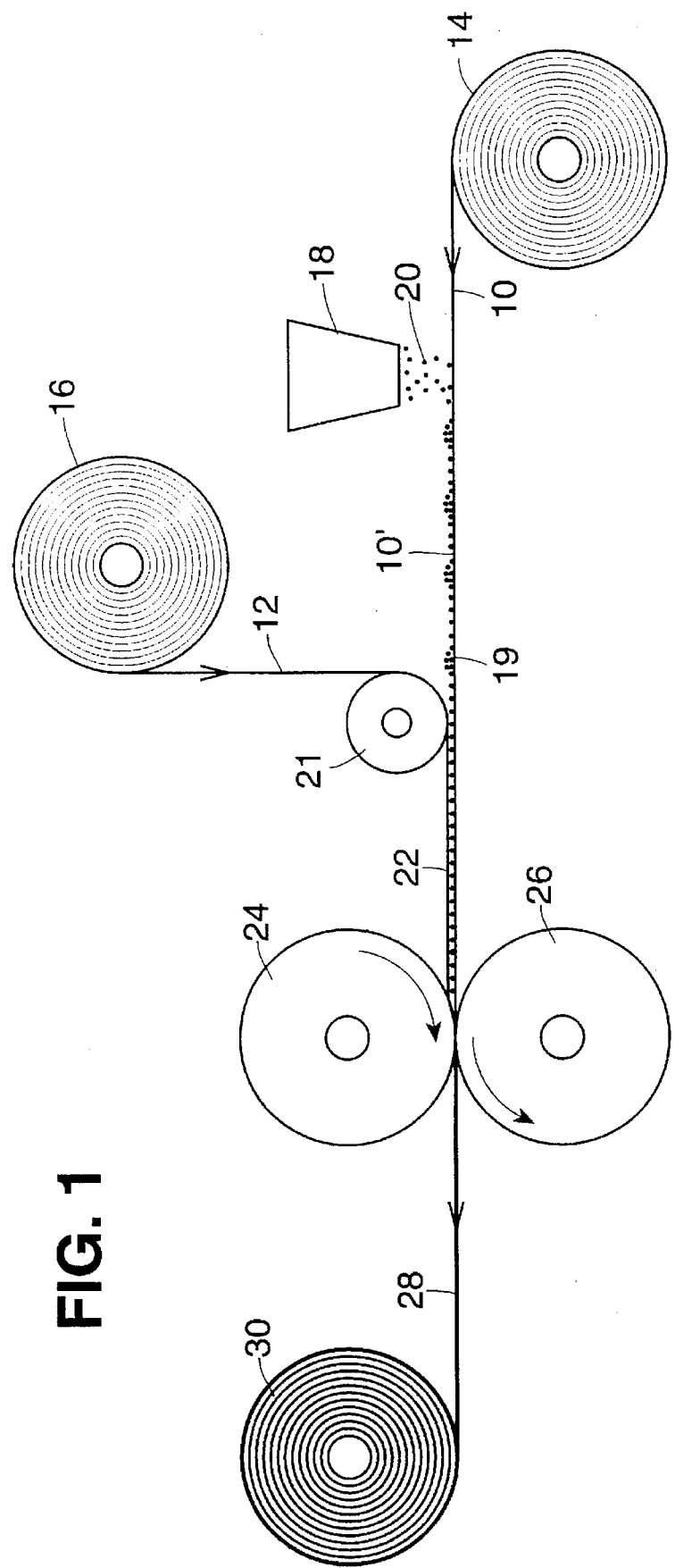
FIG. 1 is a schematic side view of the production equipment for carrying out a prior art method for producing a dental adhesive product.
Figure 2:
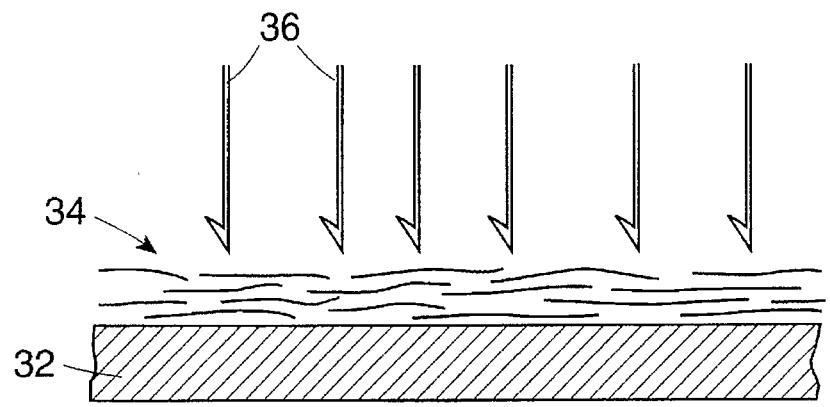
FIG. 2 is an enlarged cross-sectional view of the components of each web prior to producing a fiber-faced web.
Figure 3:
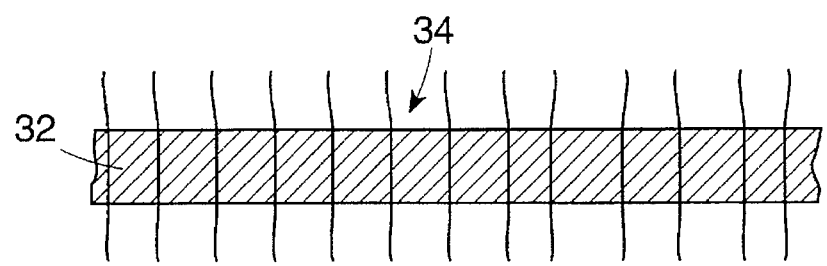
FIG. 3 is a cross-sectional view of the web of FIG. 2 after the fiber-faced web has been formed.

Referring to FIG. 2, a fiber-faced web is to be formed by placing in position an elongated sheet of cellulosic paper 32 as a carrier and then arranging thereon loose synthetic fibers 34. The loose fibers are then passed through the carrier by needle-punching them, as by needles 36, so the fibers assume the position illustrated in FIG. 3, wherein the fibers protrude from either side of paper 32 and are held in position by the paper which then acts as a carrier. Preferably, fiber 34 is made of a microcellulose material, such as cellulose acetate. Paper carrier 32 is preferably that made by the Dexter Corporation of Windsor Locks, Conn., known as Dexter 193 which is made of cellulose and regenerated cellulose and is often used as sausage casing. The Dexter 193 carrier weighs 0.6 ounces per square yard, to which 0.9 to 1.2 ounces per square yard of the cellulose acetate fiber is added, so as to bring the total weight of the paper web to 1.5 to 1.8 ounces per square yard. Another material which has also been found to be suitable for carrier 32 is a light polypropylene scrim.

It should be appreciated that the fiber-faced webs need not be the unwoven needle-punched webs of the preferred embodiment. The invention also envisions use of other materials such as simple non-woven webs or even of woven napped materials. Additionally, the web material while advantageously using cellulose or cellulose acetate may also be produced from polypropylene, nylon, other suitable materials or appropriate combinations of the aforementioned.

Figure 4:
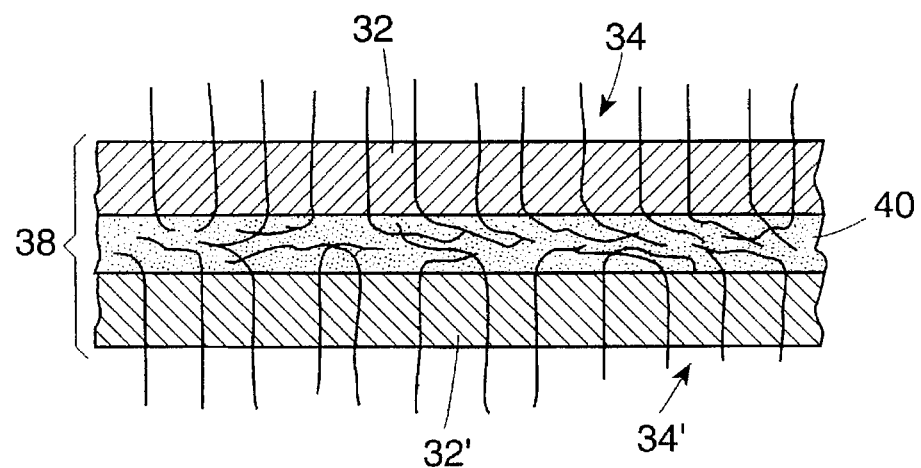
FIG. 4 is a cross-sectional view of an improved adhesive device of the invention made from the webs shown in FIG. 3.

In FIG. 4 there is illustrated a new laminated adhesive device 38. The device 38 comprises a pair of fiber-faced webs 32, 34 and 32', 34' made according to the product illustrated in FIG. 3. The web fibers are bonded together by the means of a film of a thermoplastic bonding material 40 as illustrated, to which a fixative may be optionally added as is more particularly described by the method disclosed hereinafter.

Figure 5:
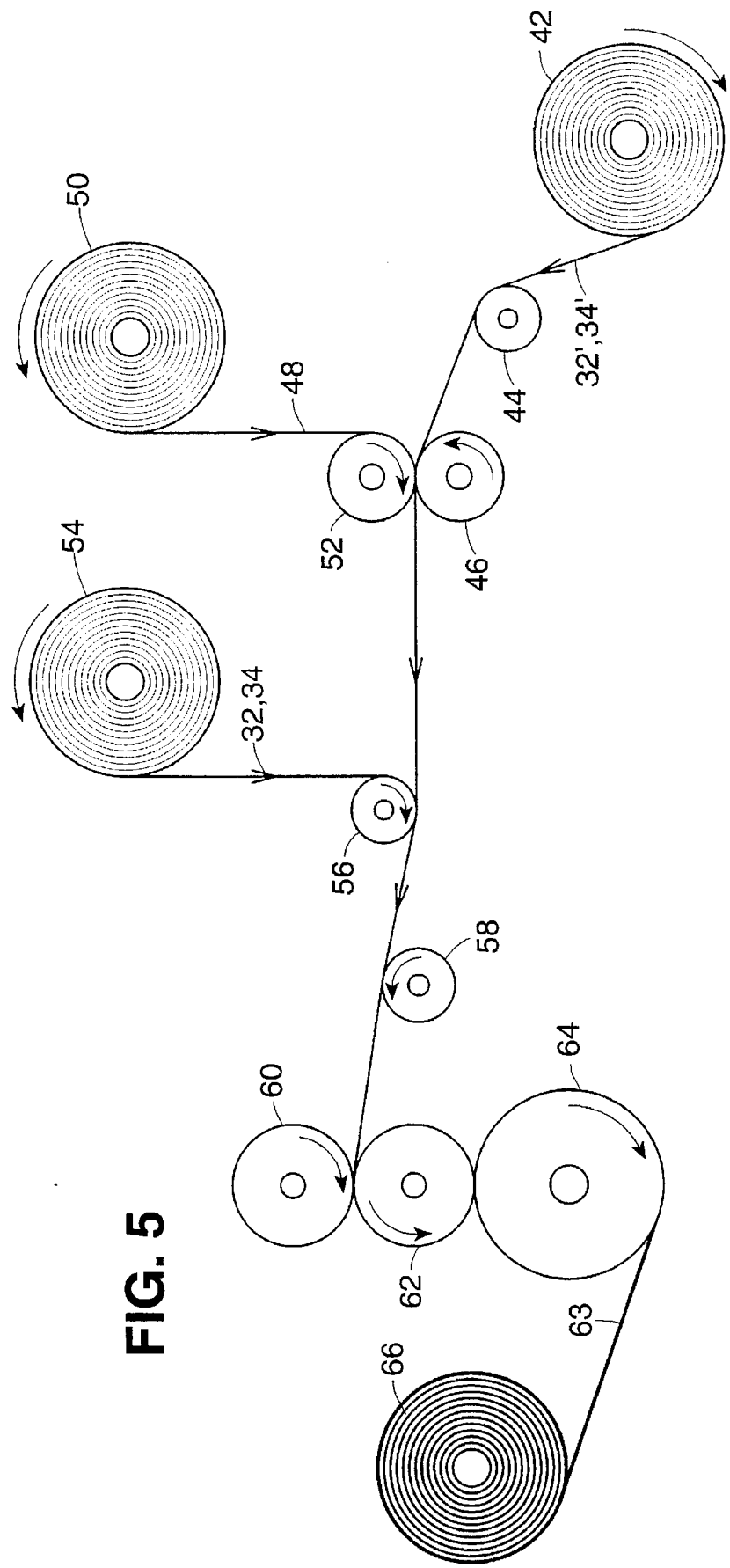
FIG. 5 is a schematic side view of the production equipment for conducting the improved method of the invention to produce the improved dental adhesive product.

By referring to FIG. 5 the process for making the product may be more readily understood. Prior to the conducting of the hereinafter described method, fiber-faced webs 32, 34 and 32', 34' may have been made and put up as a roll of material for use in the process. A web 32', 34' is fed from roll 42 over idler roll 44 horizontally over guide roll 46. Prior to conducting the instant process a cast film 48 of ethylene oxide polymer is put up as a roll of material for use in the process. The cast film 48 is fed from roll 50 under idler roll 52 and onto the surface of web 32', 34'. The upper web 32, 34 is fed from a roll 54 under an idler roll 56 to be superimposed above and in contact with web 32', 34' so that the bonding film 48 is therebetween. The superimposed webs are fed over an idler roll 58 and between a pair of calendar rolls 60, 62 heated to about 210° F., wherein the fibers of the webs 32, 34 and 32', 34' are bonded to the melted film 48 into a unitary laminate 63 which is withdrawn about a guide roll 64 and coiled up as at 66. In passing between the calendar rolls 60, 62, the ethylene polymer film partially melts and deforms to bond the fibers 34, 34' in the carriers 32, 32' and to bond the webs together. No moisture is added other than that which is incidently present in the web or in the ethylene oxide polymer.

It is contemplated that the film of ethylene oxide polymer as employed herein is preferably a cast, self-supporting film. Such a cast film is commercially available under the tradename QSP film distributed by Watson Foods in a film thickness of 3.5 mil.

If desired, the cast film can be prepared by solubilizing polyethylene oxide powder in a volatile solvent, as well as in water; coating the solution on a roll; employing a doctor blade to control the thickness of the film and evaporating the volatile solvent to deposit the film. The film can also be formed from other conventional film-forming techniques, such as spraying an ethylene oxide polymer solution onto a substrate and then drying or by dipping a substrate in a tank containing an ethylene oxide polymer solution to form a coating on the substrate and then drying the coating.

In general, the thickness of the cast film should be sufficient for manufacturing purposes and to adequately bond the superimposed fiber-faced webs. For this and other purposes the film thickness is preferably from about 0.5 to 5 mil.

Figure 6:
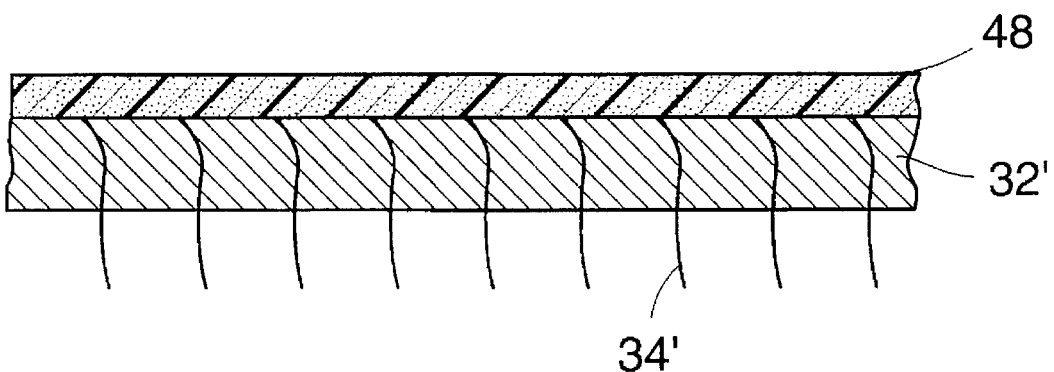
FIG. 6 is an enlarged cross-sectional view of a cast film supported on a fiber-faced web.
Figure 7:
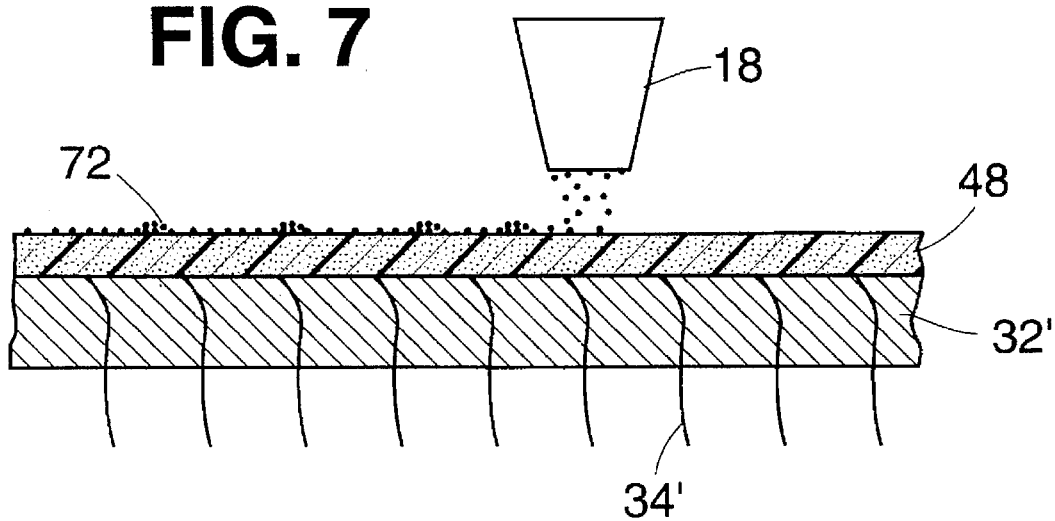
FIG. 7 is an enlarged cross-sectional view of a cast film supported on a fiber-faced web with a powder layer of water-activated adhesive thereon.

Dry water-activated adhesives are also advantageously employed in conjunction with the ethylene oxide polymer. These adhesives may be utilized in combination with the instant cast film in various forms. In one aspect, a cast ethylene oxide polymer film 48 supported on web 32', 34' as in FIG. 6 is formed. Thereafter, a powder spreader 18 is utilized to deposit a powder layer 72 of dry-water activated adhesive on the cast film 48 as in FIG. 7 prior to superimposing web 32, 34 thereon as in FIG. 5.

Figure 8:
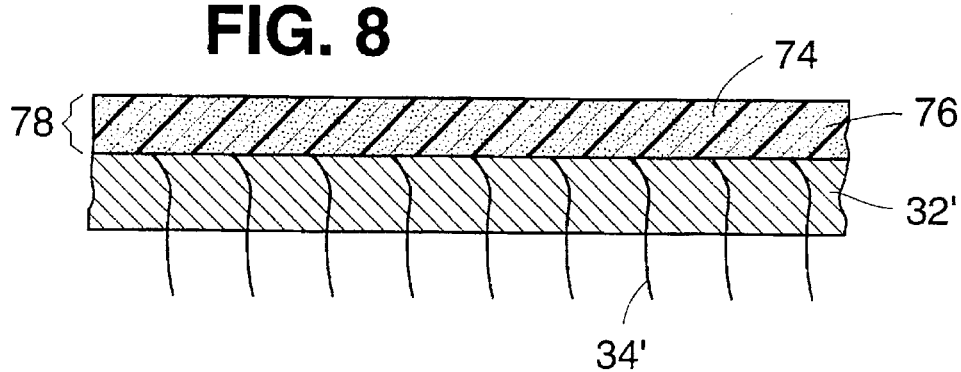
FIG. 8 is an enlarged cross-sectional view of a cast film containing a dispersed water-activated adhesive therein supported on a fiber-faced web.
Figure 9:
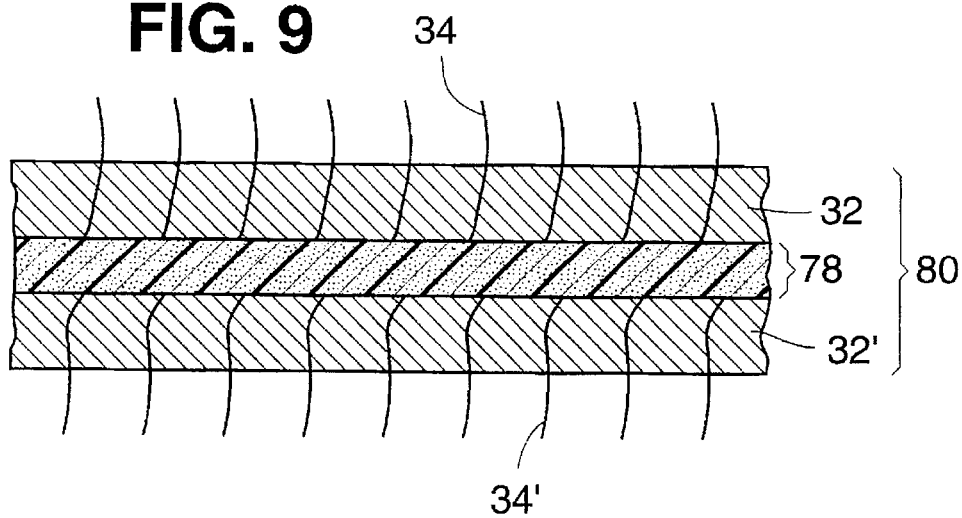
FIG. 9 is an enlarged cross-sectional view of a precursor to the improved adhesive device.

In a more preferred embodiment as shown in FIGS. 8 and 9, a dry water-activated adhesive is uniformly dispersed in particulate form 74 in the cast ethylene oxide polymer film 76 prior to application to the fiber-faced web 32', 34'. An appropriate amount of dry water-activated adhesive powder may be added to an ethylene oxide polymer solution and mixed to form a uniform dispersion thereof. The solvent is evaporated to form a cast film 78 of an ethylene oxide polymer matrix containing a water-activated adhesive uniformly dispersed in the matrix. The cast film having adhesive uniformly dispersed therein 78 is applied to web 32', 34' in the same manner as film 48 is applied to web 32', 34' employing feed roll 50, guide roller 52 and idler roller 46 as in FIG. 5. Thereafter, the upper web 32, 34 is superimposed employing idler roller 56 and the resulting precursor 80 as shown in FIG. 9 is conducted between heated calendaring rolls 60 and 62 to fuse the webs and fibers together as a unitary laminate.

Figure 10:
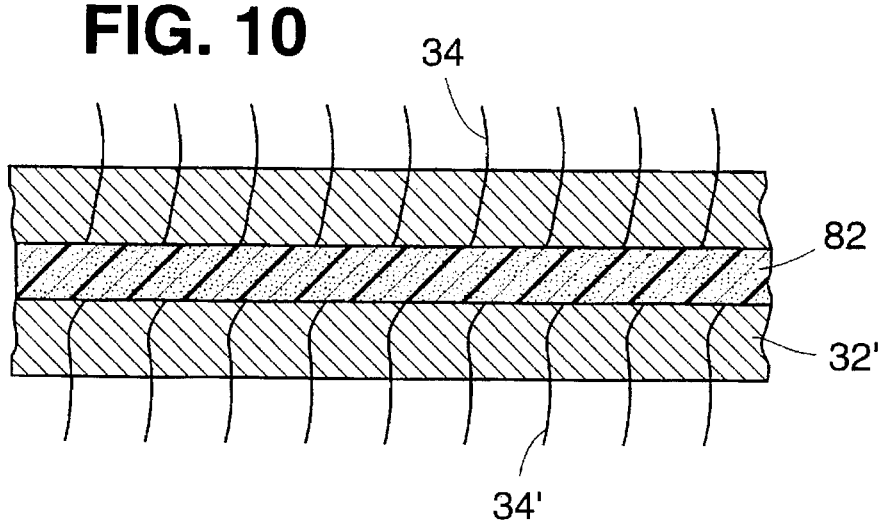
FIG. 10 is an enlarged cross-sectional view of another precursor to the improved adhesive device.

In another preferred embodiment as illustrated in FIG. 10 the water-activated adhesive may be added in solution to a solution of ethylene oxide polymer or added as a melt to a melt of ethylene oxide polymer. The resulting liquid mix of water-activated adhesive and ethylene oxide polymer is then cast as a film 82, rolled onto a feed roll 50 and utilized in the process of FIG. 5 to form a precursor to the adhesive device.

The water-activated adhesive may be any of many well-known adhesives, and preferably comprises from 0% to approximately 90% by weight of the ethylene oxide polymer/water-activated adhesive mixture. Sodium alginate has been used as the water-activated adhesive with much success. Additionally, materials such as cellulose gum, sodium carboxymethyl cellulose, methyl cellulose, polyvinyl methyl ether maleate, gelatin, pectin, karaya and tragacanth, among others, can each be used as the adhesive in combination with the sodium alginate or in its stead. Of course, suitable combinations of the adhesives may also be used.

Referring to the process illustrated in FIG. 5 in the preferred embodiment, a solution of the bonding agent, ethylene oxide polymer is admixed with sodium alginate powder and the solution or dispersion is then cast into a film. This film is a 50—50 weight blend of Kelvis-brand sodium alginate and polyox WSR-301 ethylene oxide polymer. Other polyoxyethylene oxides of different molecular weights may be used, such as polyox WSR-205, WSR-1105, and also mixtures thereof. The cast film is applied to bottom web 32', 34'. The amount of the alginate/polyox film on the web is closely controlled at 1.5 ounces of the polymers per square yard of the web.

A solution of ethylene oxide polymer powder is also admixed with a mixture of polyvinyl methyl ether-maleate and pectin. The ethylene oxide powder is 15% by weight, the polyvinyl methyl ether-maleate 65% and pectin 20% by weight. The resulting dispersion is cast into a film of ethylene oxide polymer matrix containing dispersed polyvinyl methyl ether-maleate and pectin. The film is applied to the top of web 32', 34' at 1.5 ounces of solids per square yard of the web.

Ethylene oxide powder is also admixed with a mixture of sodium alginate and methyl cellulose. The chemicals have weight percentages respectively of 65, 15 and 20. The blend is dissolved with an appropriate solvent and cast into a film. The film is applied to a web at a rate of 1.5 ounces of solids per square yard of the web.

In all of the above examples, web 32, 34 is fed from a roll 54, under an idler roll 56 and superimposed above and in contact with web 32', 34' with the cast film in between. The superimposed webs are fed over idler roll 58 and between heated calendar rolls 60 and 62 to deform the thermoplastic ethylene oxide polymer by heat and pressure and to form the resulting products.

The weight of the resulting product of the examples discussed above is 5.1 ounces per square yard, with reasonable tolerances. Of this 3.6 ounces are the webs (two pieces of 1.8 ounces each), and 1.5 ounces is ethylene oxide polymer or the water-activated adhesive/ethylene oxide polymer blend. The thickness of the product is about 0.015 to 0.018 inches. The temperature of the heated calendar rolls 60, 62 is approximately 210° F., which is sufficient to melt the ethylene oxide polymer, but low enough to not affect or soften the web or the water-activated adhesives. The resulting products are dental adhesive laminates with excellent characteristics. The products are expected to hold together longer than the previous products of the prior art, and the products better retain the water-activated adhesives so as to permit the dental adhesion products to more effectively operate.

The product is typically 45 inches wide, then slit to 22½ inches wide for convenient handling. Typically, the product is rolled up on cores for shipment. No drying or other processing is conducted; nor are other chemicals added. The rollgoods are thereafter die-cut into the appropriate shapes for use as dental adhesives and packed for sale.

Although a preferred embodiment and other examples of the process and product thereof have been described, it will be evident that changes may be made in the steps of the process and components and details of the product without departing from the spirit and principles of the inventions.

What is claimed is:

1. A method of producing a dental adhesive product comprising:
    (a) applying a film comprising a thermoplastic ethylene oxide polymer composition to a surface of a first fibrous web;
    (b) contacting the first web with a second fibrous web in superimposed relation; and
    (c) applying heat and pressure to deform the ethylene oxide polymer composition and thereby thermoplastically bond the webs into a unitary structure.

2. The method of claim 1 in which a dry water-activated adhesive is additionally applied to a region between the fibrous webs prior to step (b).

3. The method of claim 2 in which the dry water-activated adhesive is applied as a powder layer on a surface of the film.

4. The method of claim 2 in which the dry water-activated adhesive is dispersed in powder form in the ethylene-oxide polymer composition prior to applying the film to the surface of the first fibrous web.

5. The method of claim 2 in which a film of a uniform composition of thermoplastic ethylene oxide polymer and said water-activated adhesive is formed prior to applying the film to the surface of the first fibrous web.

6. The method of claim 1 in which the film has a thickness from 0.5 to 5 mil.

7. The method of claim 1 comprising the step of inserting a plurality of synthetic fibers into said first and second fibrous webs so that the fibers extend transversely through the webs prior to step (a), whereby the webs and fibers are both bonded into said unitary structure.

8. The method of claim 1 wherein the dry water-activated adhesive is sodium alginate.

9. The method of claim 1 in which at least one of said webs is cellulose paper having protruding fibers of cellulose acetate.

10. The product of the method according to any one of claims 1–9.

11. A dental adhesive product comprising a pair of superimposed fiber-faced webs, each web having a carrier portion with fibers held therein and protruding therefrom to present a fiber facing on each side of each of said webs and a film comprising an ethylene oxide polymer composition sandwiched between said webs, wherein said film having been deformed by application of heat and pressure thereby thermoplastically bonds the webs into a unitary structure.

12. The dental adhesive product of claim 11 in which a dry water-activated adhesive is additionally present between said webs.

13. The dental adhesive product of claim 12 in which the dry water-activated adhesive is present as a powder layer.

14. The dental adhesive product of claim 12 in which the dry water-activated adhesive is dispersed as a powder in the film.

15. The dental adhesive product of claim 12 in which the dry water-activated adhesive and the ethylene oxide polymer together form the composition of the film.

16. The dental adhesive product of claim 12 in which said dry water-activated adhesive is sodium alginate.

* * * * *

UNITED STATES PATENT AND TRADEMARK OFFICE
CERTIFICATE OF CORRECTION

PATENT NO. : 5,624,745
DATED : April 29, 1997
INVENTOR(S) : HERBERT LAPIDUS

It is certified that error appears in the above-identified patent and that said Letters Patent is hereby corrected as shown below:

ON THE TITLE PAGE:

AT [56] REFERENCES CITED

U.S. PATENT DOCUMENTS

"Nedig" should read --Nedwig--.

COLUMN 1

Line 20, "plastic" should read --thermoplastic--.

UNITED STATES PATENT AND TRADEMARK OFFICE
CERTIFICATE OF CORRECTION

PATENT NO. : 5,624,745
DATED : April 29, 1997
INVENTOR(S) : HERBERT LAPIDUS

It is certified that error appears in the above-identified patent and that said Letters Patent is hereby corrected as shown below:

<u>COLUMN 2</u>

```
Line 16, "equipment:" should read --equipment--.
Line 43, "use fulness." should read --usefulness.--.
```

Signed and Sealed this

Twenty-third Day of December, 1997

Attest:

BRUCE LEHMAN

Attesting Officer

Commissioner of Patents and Trademarks

UNITED STATES PATENT AND TRADEMARK OFFICE
CERTIFICATE OF CORRECTION

PATENT NO. : 5,624,745

DATED : April 29, 1997

INVENTOR(S) : HERBERT LAPIDUS

It is certified that error appears in the above-identified patent and that said Letters Patent is hereby corrected as shown below:

On the title page,
 AT [56] REFERENCES CITED

U.S. PATENT DOCUMENTS
      Insert: --Re 33093 10/1989 Schiraldi--.

Signed and Sealed this

Twenty-eighth Day of April, 1998

Attest:

BRUCE LEHMAN

Attesting Officer

Commissioner of Patents and Trademarks